United States Patent [19]
Garrill et al.

[11] Patent Number: 6,119,853
[45] Date of Patent: Sep. 19, 2000

[54] METHOD AND PACKAGE FOR STORING A PRESSURIZED CONTAINER CONTAINING A DRUG

[75] Inventors: Karl Andrew Garrill, Hertford, United Kingdom; Richard J. Haan, Germantown, Tenn.; Craig Steven Herman, Raleigh, N.C.; Richard Ian Walker, Hertford, United Kingdom

[73] Assignee: Glaxo Wellcome Inc., Research Triangle Park, N.C.

[21] Appl. No.: 09/216,183

[22] Filed: Dec. 18, 1998

[51] Int. Cl.[7] ................................... B65D 30/02
[52] U.S. Cl. .................... 206/204; 206/438; 206/439; 383/113
[58] Field of Search ..................... 206/204, 363, 206/438, 439, 484.1, 570; 383/113

[56] References Cited

U.S. PATENT DOCUMENTS

| | | | |
|---|---|---|---|
| 4,509,196 | 4/1985 | Sak et al. | 206/438 |
| 4,874,090 | 10/1989 | Dyke | 206/439 |
| 5,718,355 | 2/1998 | Garby et al. | 206/459.1 |
| 5,833,066 | 11/1998 | Hargus et al. | 206/438 |

*Primary Examiner*—Jim Foster
*Attorney, Agent, or Firm*—Christopher P. Rogers

[57] ABSTRACT

A method and package for storing a pressurized container which is filled with a drug formulation at a predetermined pressure. The drug formulation includes a mixture of a drug and a propellant. The package which encloses the pressurized container substantially prevents ingression of water vapor and particulate matter into the package while permitting egression of the propellant which may leak from the pressurized container.

30 Claims, 3 Drawing Sheets

METHOD AND PACKAGE FOR STORING A PRESSURIZED CONTAINER CONTAINING A DRUG

BACKGROUND OF THE INVENTION

1. Field of the Invention

The present invention relates to a method and package for storing a pressurized container containing a drug.

2. Description of the Background Art

For environmental reasons, there has been a move to replace chlorofluorocarbons (CFCs) (also simply known as "fluorocarbons") such as P11, P114 and P12 with hydrofluoroalkane propellants such as HFC-134a and HFC-227. When these fluorocarbon propellants are used as a propellant in a pressurized drug delivery system, various technical problems can occur with various drug formulations. Also, it is necessary to modify the construction of metered dose inhalers for optimum stability and aerosol formation.

One storing mechanism for a metered dose inhaler (MDI) uses a plastic tube which has a resealable lid to close the tube. The resealable lid for this tube employs a desiccant to absorb moisture present in the tube.

Such plastic tubes typically increase manufacturing cost and require complex and/or expensive manufacturing processes. Such tubes are frequently bulky in that they require a significant amount of storage space relative to the size of the container disposed within the plastic tube.

SUMMARY OF THE INVENTION

Accordingly, a need in the art exists for a method and package for storing a pressurized container filled with a propellant and a drug which substantially prevents ingression of water vapor and particulate matter into the storage package while permitting egression of the propellant to increase shelf life and performance of the drug and the propellant. Furthermore, a need exists in the art to provide a method and package for storing a pressurized container filled with a drug and a propellant which is cost effective and which does not require complex manufacturing processes and which in turn efficiently envelopes the container to maximize available storage space.

It is a primary object of the present invention to provide a method and package for storing a pressurized container, where the pressurized container is filled with a drug and a propellant and where the method and package substantially prevent ingression of water vapor and particulate matter into the package while permitting egression of the propellant whereby shelf life of the drug is prolonged and performance of the drug and the propellant are maintained or increased.

It is a further object of the present invention to provide a method and package for storing a pressurized container filled with a drug and a propellant where the method and package substantially absorb residual moisture in the package enclosing the pressurized container that is sometimes present on the outer surface of the pressurized container prior to sealing pressurized container within the package.

Another object of the present invention is to provide a method and package for storing a pressurized container including a drug and a propellant which substantially reduces manufacturing costs while substantially reducing the complexity of the manufacturing process of the package.

Another object of the present invention is to provide a method and package for storing a pressurized container having a drug and a propellant which is easily opened and readily disposable.

It is a further object of the present invention to provide a method and package for storing a pressurized container having a drug and a propellant, whereby the propellant preferably meets governmental guidelines which prohibit the use of CFCs.

Another object of the present invention is to provide a method and package for storing a pressurized container which includes a drug and a propellant that does not require complex mechanical devices to envelope or enclose the pressurized container while substantially reducing the amount of storage space needed for the pressurized container where the package substantially conforms to the shape of the pressurized container. The package is amorphous in shape due to the flexible materials from which it is made.

Another object of the present invention is to provide a method and package which form an enclosed volume that stores a pressurized container in a controlled environment where the pressurized container is isolated from harmful environmental conditions such as humidity, dust, light, and water vapor and other particulate matter.

Another object of the present invention is to provide and article of manufacture comprising an integral aerosol dispensing apparatus, a drug formulation, and a flexible package. It is further an object of the present invention to provide a drug formulation and carrier with packaging material having labeling and information relating to the composition contained therein and printed thereon. Additionally, a further object of the invention is to provide an article of manufacture having a brochure, report, notice, pamphlet, or leaflet containing product information.

These and other objects of the present invention are fulfilled by providing a container storage system comprising: a drug formulation comprising a mixture of a drug and a propellant; a pressurized container filled with the drug formulation at a predetermined pressure; and a flexible package for wrapping and sealing the pressurized container providing an enclosed volume in which the pressurized container is disposed, the flexible package being impermeable to water vapor and permeable to the propellant, the flexible package substantially preventing ingression of water vapor and particulate matter into the enclosed volume while permitting egression of the propellant.

In addition, these and other objects of the present invention are also accomplished by providing a method of storing a container comprising the steps of: providing a flexible package material, which is impermeable to water vapor and permeable to a propellant; filling a container with a drug formulation comprising a drug and the propellant at a predetermined pressure; wrapping the container with the flexible package material to form an enclosed volume in which the container is disposed therein; and sealing the flexible package which in turn closes said enclosed volume, the flexible package substantially preventing ingression of water vapor and particulate matter into the enclosed volume while permitting egression of the propellant from the enclosed volume.

Moreover, these and other objects of the present invention are fulfilled by a packaged metered dose inhaled comprising: an MDI comprising a container and a drug metering valve, a pressurized drug formulation in the container comprising a propellant and a drug dispersed or dissolved in the propellant; and an overwrap of flexible material enclosing said MDI, the overwrap being made of a moisture impermeable material.

Also, these and other objects of present invention are accomplished by providing an article of manufacture comprising: an aerosol dispensing apparatus for dispensing metered amounts of fluid material from a reservoir, the apparatus comprising a container defining a reservoir, and a dispensing valve; the dispensing valve comprising: a metering chamber body defining a metering chamber and having one or more metering chamber ports; and a stem allowing for slideable movement within the metering chamber body, the stem having a dispensing passage and being connected to a sealing segment allowing for slideable movement over the one or more metering chamber ports, the sealing segment being moveable such that in a first position the metering chamber is fluidically isolated from the dispensing passage; and the metering chamber is in fluidic communication with the reservoir through the one or more metering chamber ports and the dispensing passage; and in a second position the metering chamber is in fluidic communication with the dispensing passage; and the metering chamber is fluidically isolated from the reservoir by the sealing segment occluding the one or more metering chamber ports; a drug formulation located within the aerosol dispensing apparatus comprising a safe and effective medicament and a pharmaceutically acceptable propellant; and a flexible package for wrapping and sealing the container providing an enclosed volume in which said pressurized container is disposed, the flexible package being impermeable to water vapor and permeable to the propellant, the flexible package substantially preventing ingression of water vapor and particulate matter into the enclosed volume while permitting egression of the propellant.

These and other objects of the present invention are also accomplished by providing a method of improving a product performance comprising the steps of: providing a flexible package material made of at least one heat sealable layer, at least one layer of a metal foil, and a protective layer; the flexible package material being impermeable to water vapor and permeable to a propellant; filling a container with a drug formulation comprising a drug and the propellant at a predetermined pressure; wrapping the container with the flexible package material to form an enclosed volume in which the container is disposed therein; and sealing the flexible package which in turn closes the enclosed volume, the flexible package substantially preventing ingression of water vapor and particulate matter into the enclosed volume while permitting egression of the propellant from the enclosed volume.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Pressurized Containers

The pressurized containers useful in the invention include any containers in which a drug and a propellant can be stored. The pressurized container is preferably an MDI or an MDI can. The term "metered dose inhaler" or "MDI" means a unit comprising a can, a crimped cap covering the mouth of the can, and a drug metering valve situated in the cap, while the term "MDI system" also includes a suitable channeling device. The term "MDI can" means the container without the cap and valve. The term "drug metering valve" or "MDI valve" refers to a valve and its associated mechanisms which delivers a predetermined amount of drug formulation from an MDI upon each activation. The channeling device may comprise, for example, an actuating device for the valve and a cylindrical or cone-like passage through which medicament may be delivered from the filled MDI can via the MDI valve to the nose or mouth of a patient, e.g. a mouthpiece actuator. The relation of the parts of a typical MDI is illustrated in U.S. Pat. No. 5,261,538 incorporated herein by reference. A suitable MDI is disclosed in WO 96/26755, the entire contents of which is hereby incorporated by reference. Preferred pressurized containers for use in MDIs are disclosed in WO 96/32151, WO 96/32345, WO 96/32150 and WO 96/32099.

The pressurized container 34 is preferably a vial made from stainless steel. However, other materials are not beyond the scope of the present invention. Other materials for the pressurized container 34 include, but are not limited to, ferrous alloys, non-ferrous alloys, ceramic materials, polymers, composite materials, and mixtures thereof. Suitable containers which contain a polymeric coating on the inside thereof are disclosed in WO 96/32151.

Drugs

Preferred drugs (also referred to as "medicaments") and drug combinations are disclosed in WO 96/32151, WO 96/32345, WO 96/32150 and WO 96/32099, the entire contents of which are hereby incorporated by reference. These drugs include, for example, fluticasone propionate or a physiologically acceptable solvate thereof, beclomethasone dipropionate or a physiologically acceptable solvate thereof, salmeterol or a physiologically acceptable salt thereof and albuterol or a physiologically acceptable salt thereof. Medicaments may be selected from, for example, analgesics, e.g. codeine, dihydromorphine, ergotamine, fentanyl or morphine, anginal preparations, e.g. diltiazem; antiallergics, e.g. cromoglycate, ketotifen or nedocromil; antiinfectives e.g. cephalosporins, penicillins, streptomycin, sulphonamides, tetracyclines and pentamidine; antihistamines, e.g. methapyrilene; antiinflammatories, e.g. beclomethasone (e.g. the dipropionate), flunisolide, budesonide, tipredane or triamcinolone acetonide; antitussives, e.g. noscapine; bronchodilators, e.g. salbutamol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, orciprenaline, or (-)-4-amino-3,5-dichloro-α-[[[6-[2-(2-pyridinyl)ethoxy]hexyl]- amino]-methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimise the activity and/or stability of the medicament and/or to minimize the solubility of the medicament in the propellant.

Additionally, any suitable combination of drugs can be used in the present invention. For example, Seretide (fluticasone and Serevent) can be used in the present invention.

Propellants

"Propellants" used herein mean pharmacologically inert liquids with boiling points from about room temperature (25° C.) to about −25° C. which singly or in combination exert a high vapor pressure at room temperature, including CFCs such as Freon and hydrofluorocarbons. Upon activation of the MDI system, the high vapor pressure of the propellant in the MDI forces a metered amount of drug formulation out through the metering valve then the propellant very rapidly vaporizes dispersing the drug particles. The propellants used in the present invention are low boiling fluorocarbons; in particular, hydrofluorocarbons or hydrofluoroalkanes such as HFC-134a and HFC-227. The invention is particularly useful with propellants (including propellant mixtures) which are more hygroscopic than P11, P114 and/or P12 such as HFC-134a and HFC-227.

Flexible Packaging Materials

The flexible packaging material can be any material which is impervious to or substantially impervious to moisture. The packaging material is preferably permeable to propellants such as HFC-134a and/or HFC-227 whereby if the propellant slowly leaks from the pressurized container, the propellant will slowly pass, by diffusion or otherwise, through the packaging material.

For ease of manufacturing, and in order to provide the necessary properties to the packaging material, the flexible packaging material preferably comprises a non-thermoplastic substrate (such as a metal foil or a polymer such as a polyester) and a heat sealable layer disposed thereon. The heat sealable layer is usually disposed on the inner surface of the assembled package. The substrate may also have an additional protective layer on the surface opposite the heat sealable layer. An example of a particularly useful foil laminate is a polyester film adhesively laminated to aluminum foil adhesively laminated to Ionomer (SURLYN™) film, for example, 12 $\mu$ polyester/9 $\mu$ aluminum/50 $\mu$ ionomer film supplied by Lawson Mardon Singen (LMS).

The substrate is preferably formed from a metal foil. However, other metals for the substrate include, but are not limited to, tin, iron, zinc, or magnesium formed on a sheet by vacuum deposition or sputtering and a carboxyl group-containing polyolefin layer formed on the metal layer by lamination.

The heat sealable layer can be formed from any thermoplastic or thermosetting material such as an ionomer resin. Ionomer resins typically include ionically cross-linked ethylene-methacrylic acid and ethylene acrylic acid copolymers. Properties which distinguish these ionomers resins from other polyolefin heat-sealed polymers are high clarity, high impact resistance, low haze in lamination, tear resistance, abrasion resistance, solid state toughness, and moisture imperviousness. In the preferred embodiment, the heat sealable layer is made out of SURLYN™ (an ionomer resin) or a form of polyethylene to provide sufficient heat sealing properties.

The outer protective layer, if present, can be formed of any material as long as the final laminate has the requisite properties.

Preferably, the protective layer (e.g., polyester) is adhesively laminated to the substrate (e.g., aluminum) and the substrate layer in turn is adhesively laminated to the heat sealable layer (e.g., the ionomer film or SURLYN™ (an ionomer resin)).

Preferred exemplary thicknesses of the three layers include a protective layer 1 to 40, preferably 4 to 30, more preferably 10 to 23 microns, and most preferably 12 microns; a substrate layer of 1 to 100, preferably 3 to 70, more preferably 5 to 50 microns, more preferably 6 to 20 microns, and most preferably 9 microns. For the heat sealable layer, preferred exemplary thicknesses include thicknesses of 1 to 100, preferably 5 to 70, more preferably 10 to 60, more preferably 20 to 55 microns, and most preferably 50 microns.

Adhesives may be used to join the respective layers of materials together. The adhesive layers are typically substantially smaller in thickness relative to the thickness of the substrate, heat sealable and/or protective layers which they bond.

The number, size, and shape of the layers are not limited to those layers shown in the drawings. Any number of layers with relative areas of any size and predetermined thicknesses may be used so long as the flexible package forms an enclosed volume which substantially prevents ingression of water vapor and particulate matter into the enclosed volume while permitting egression out of the enclosed volume of any propellant leaving the pressurized container. The size, shape, and number of layers of the package is typically a function of the size and contents of the pressurized container which includes a drug and a propellant.

The package is believed to operate similarly to a virtual one-way valve due to the composition of the layers and due to the transmission rate of water vapor molecules into the enclosed volume relative to the transmission rate of gas molecules of a propellant, such as a hydrofluoroalkane, out of the enclosed volume. The package permits the propellant in the pressurized container to diffuse out of the enclosed volume while substantially preventing water vapor and other particulate matter from entering the enclosed volume. Excess or leakage of the propellant is permitted to egress from the package. The virtual one-way valve function of the package prevents or minimizes the chance of any sudden ruptures or prevents or minimizes unexpected expulsion of the propellant during opening of the package.

Moisture Absorbing Materials

The moisture absorbing material is preferably a silica gel desiccant sachet. However, other vapor or moisture absorbing mechanisms are not beyond the scope of the present invention. Other vapor or moisture absorbing materials include desiccants made from inorganic materials such a zeolites and aluminas. Such inorganic materials of vapor or moisture absorbing materials have high water absorption capacities and favorable water absorption isotherm shapes. The water absorption capacity of such materials typically varies from 20 to 50 weight percent.

In the preferred embodiment, the absorbing material is a MINIPAX® supplied by Multisorb Technologies in the United States and Silgelac in Europe (silica gel packaged inside TYVEK®, which is a nylon mesh bonded with a microporous polyurethane). Other exemplary moisture absorbing materials include, but are not limited to, alumina, bauxite, anhydrous, calcium sulfate, water-absorbing clay, activated bentonite clay, a molecular sieve, or other like materials which optionally include a moisture sensitive color indicator such as cobalt chloride to indicate when the desiccant is no longer operable. While in the preferred embodiment of the present invention, the package is designed to substantially prevent ingression of water vapor and particulate matter into the enclosed volume, the moisture absorbing material is placed within the enclosed volume in order to absorb any residual moisture present in the atmosphere or on the external surface of the pressurized container or mouthpiece or a combination thereof, prior to sealing the package.

The desiccant should be present in an amount sufficient to absorb any residual moisture inside the package or which might escape from inside the pressurized container. When silica gel is used, 1 g to 10 g of silica gel is sufficient for a typical MDI. Moreover, the desiccant should be present in an amount sufficient to absorb any moisture that possibly ingresses from the external environment.

The Container Storage System

Figure 1:
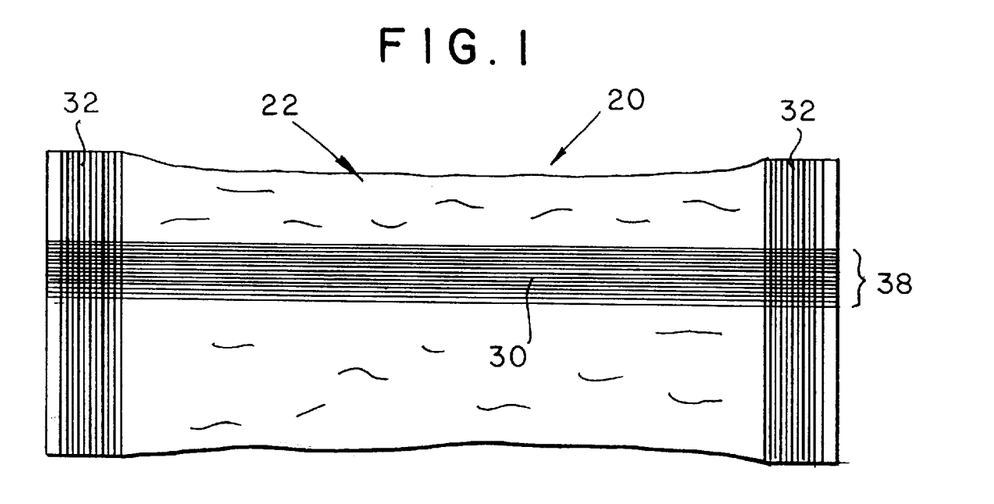
FIG. 1 is a top elevational view of the package for storing a pressurized container of the present invention.

Referring in detail to the drawings and with particular reference to FIG. 1, a container storage system (or packaged product) 20 is shown. The container storage system 20 includes a package or wrapping 22 that employs multi-layers of material 24, 26, 28. (See FIG. 4.) The package 22 further includes fin seams 30, 32 which are disposed along two parallel side edges of the package and along a single longitudinal edge of the package 22.

The number and type of fin seams 30, 32 are not limited to the types shown in the drawings. The package 22 can include additional seams or significantly fewer seams such as a continuous single seam. The orientation of the seams 30, 32 is not limited to the orientation shown in the drawings. The orientation of the seams 30, 32 is typically a function of the sealing device and such seams may be oriented in a manner which substantially increases manufacturing efficiency. During manufacture, the longitudinal seam 30 may be formed first by heat sealing and the two end seams 32 may then be formed by heat sealing to close the package. Other types of seams include, but are not limited to, gusset type seams which include excess material which provides expansibility, stitched type seams, or mechanically crimped seams, and other like structures.

Figure 3:
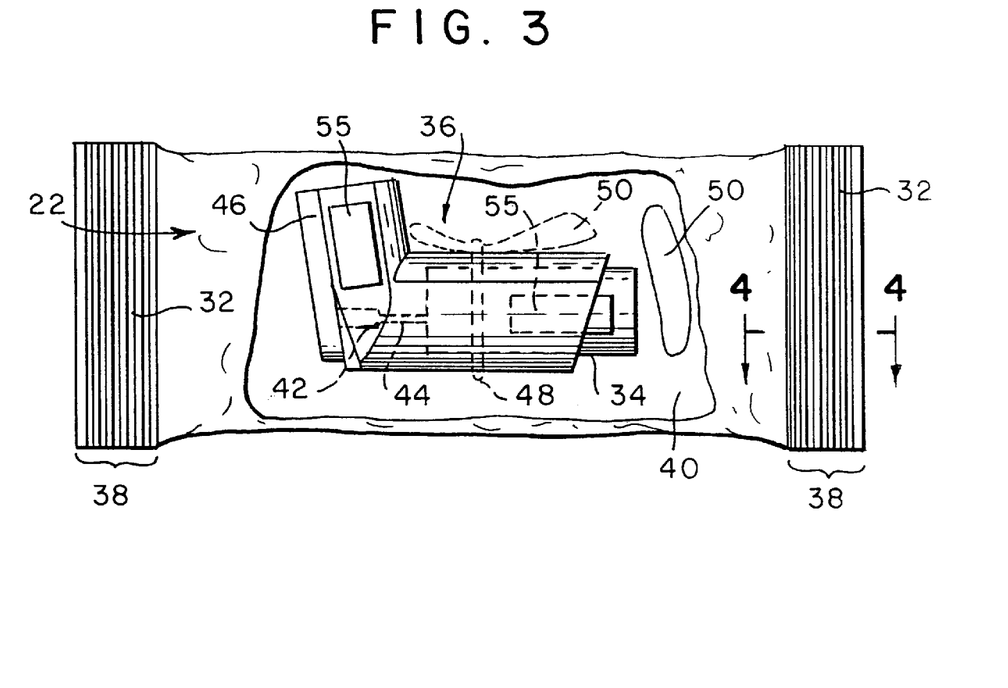
FIG. 3 is a cutaway bottom view of the package for storing a pressurized container of the present invention.

The container storage system includes a pressurized container 34 which is preferably part of an MDI 36 (see FIG. 3). While the preferred pressurized container 34 is part of an MDI 36, other devices which include pressurized containers 34 are not beyond the scope of the present invention.

The fin seams 30 and 32 are formed by a conventional heat sealing device which mechanically crimps sides of the package 22 together while simultaneously providing heat to the sides 30, 32. The heat sealing device typically has electrical heater elements shaped to produce the pattern of the fin seams 30, 32 where the fin seams include multiple ridges 38. The sealing mechanism of the container storage system 20 of the present invention is not limited to heat sealing devices. Other sealing devices include, but are not limited to, glue sealing machines, sonic welding machines, electron beam radiation machines, and other like sealing devices.

Figure 2:
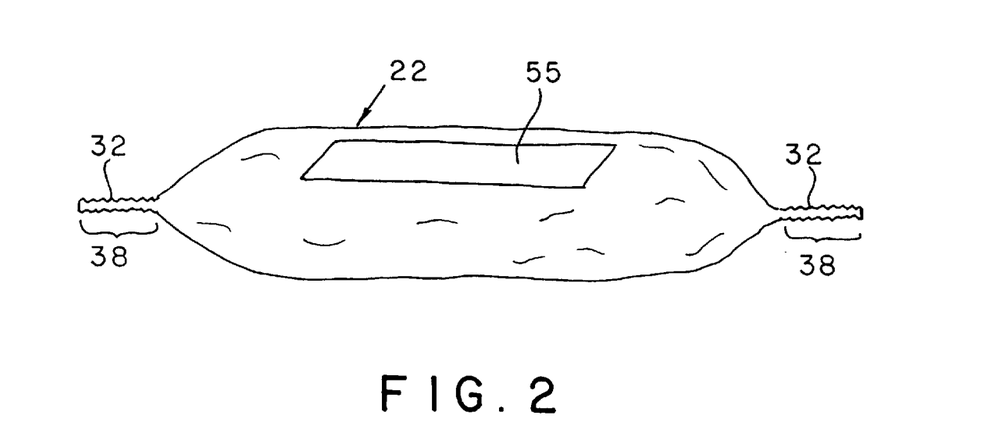
FIG. 2 is a side view of the package for storing a pressurized container of the present invention.

As seen in FIGS. 1 and 2, the package 22 preferably has a substantially rectangular configuration with a substantially elliptical cross section, however, other shapes of the package 22 are not beyond the scope of the present invention. Other shapes include, but are not limited to, circular, square, triangular, trapezoidal, pentagonal, hexagonal, octagonal, and other like shapes. The shape of the package 22 is preferably a function of the shape of the enclosed pressurized container 34 as well as the amount and type of storage space since the package 22 is made from flexible materials as will be described in further detail below.

As seen in FIG. 3, the package 22 provides an enclosed volume 40 in which the pressurized container 34 is disposed therein. The size of the enclosed volume 40 can be adjusted according to the size of the pressurized container 34 and related parts thereto. Preferably, the enclosed volume 40 is of a size which permits relative ease of closing respective sides and layers 24, 26 and 28 without substantial stretching of the package 22. The enclosed volume 40 may be substantially evacuated prior to formation of the fin seams 30, 32 to substantially reduce any water vapor being present in the enclosed volume 40. The enclosed volume 40 may be evacuated to such a degree that the enclosed volume 40 is a vacuum region around the pressurized container 34. While the enclosed volume 40, may remain constant, its relative shape may change according to shifting of the pressurized container 34 disposed within the enclosed volume 40.

The amorphous shape of the enclosed volume 40 is attributed to the flexible materials which make up the layers 24, 26, 28 of the package 22 which will be discussed in further detail below. The enclosed volume can be varied in size such that it substantially conforms to the shape of the pressurized container 34 and any related parts thereto or such that the enclosed volume 40 is larger than the pressurized container 34, as shown in FIG. 3. When the enclosed volume is of a size which is substantially equivalent with the surface area of the pressurized container 34 and related parts, the layers 24, 26, and 28 of material substantially conform to the shape of the pressurized canister 34 and related parts. The package is preferably placed in a separate, more rigid container, such as a paperboard or cardboard box 74 (See FIG. 6) typically used in the pharmaceutical industry. The package may expand during storage due to slow leakage of the propellant from the pressurized container. In this situation, the shape of the package may conform to some extent to the internal shape of the rigid container if the volume of the rigid container is just slightly larger than the expanded volume of the flexible package.

In the preferred embodiment, FIG. 3 shows the pressurized container 34 to be connected to a nozzle 42 by a valve stem 44. The pressurized container 34 is preferably a metal vial having a metering valve 60 (See FIG. 5) disposed therein which is connected to the valve stem 44. The pressurized container 34 is not limited to the nozzle 42 and valve stem 44 shown and the metering valve 60. While the pressurized container 34 preferably includes a metering valve, other valve systems are not beyond the scope of the present invention. Other valve systems include, but are not limited to, wedge gate valve systems, double-disc gate valve systems, globe and angle valve systems, swing check valve systems, end cock valve systems, and other like valve systems. Since the pressurized container 34 is preferably part of an MDI, the valve design is typically a function of providing a predetermined dosage or amount of the drug contained within the pressurized container 34 to a user.

The nozzle 42 is preferably fixably secured to the mouthpiece 46. However, other embodiments where the nozzle 42 is separate or detached from the mouthpiece 46 is not beyond the scope of the present invention. The pressurized canister 34, the nozzle 42, and the mouthpiece 46 together comprise an MDI 36.

As seen in FIG. 3, nozzle 42 is in fluid communication with the mouthpiece 46 so that upon movement of the pressurized container relative to the mouthpiece 46 in a direction where the pressurized container 34 moves towards the nozzle 42 fixed to one side of the mouthpiece 46, a metered dosage or predetermined amount of the drug and propellant contained within the pressurized container 34 is released. Such a combination of the fixed nozzle 42, mouthpiece 46, valve stem 44, and pressurized container 34 form an MDI 36 as outlined above.

In a preferred embodiment, the moisture absorbing material 50 lays adjacent to the mouthpiece 46 in a loose or free flowing manner. Alternatively, the moisture absorbing material can be secured to the inside of the flexible package. In another alternative embodiment, the moisture absorbing material may be disposed within the container 34 or attached to a bracket structure such as a ring which is fastened to the container 34.

In one possible embodiment, the moisture absorbing material may be attached to the external surface of the mouthpiece 46 by a fastening device such as a rubber band 48. The fastening device 48 is preferably a removable elastic mechanism such as a rubber band. However, other fastening devices are not beyond the scope of the present invention. Other fastening devices include, but are not limited to, adhesives, adhesive tapes, shrink-wrap plastic, fasteners such as screws, nails, or rivets, compartments which are part of the mouthpiece housing 46, and other like attachment devices.

The mouthpiece 46 substantially encloses pressurized container 34. The mouthpiece 46 is preferably simple in structure so that manufacturing efficiency and economy is substantially increased. However, other mouthpieces 46 are not beyond the scope of the present invention. Other mouthpieces include, but are not limited to, relatively movable mouthpieces with multiple parts, mouthpieces which also include a protective casing substantially surrounding the mouthpiece protecting the mouthpiece 46 from damage due to shock, and other like mouthpiece structures.

The pressurized container 34 may be held in the mouthpiece 46 by ribs or projections (not shown) extending from walls of the mouthpiece so that the pressurized container 34 is in a press-fit engagement with the mouthpiece 46. The valve stem 44 also provides a secure connection to the nozzle 42 which is fixedly secured to the mouthpiece 46. Other types of supporting mechanisms which hold the pressurized container 34 within the mouthpiece 46 are not beyond the scope of the present invention. Other types of securing or supporting mechanisms include, but are not limited to, fasteners such a screws, nails, or rivets, adhesives, mouthpieces with a female or male locking/keying mechanism which engages with a predetermined shape of the pressurized container, or other like supporting structures.

In the preferred embodiment of the invention, the support mechanisms, such as ribs or projections (not shown) of the mouthpiece 46 are designed for manufacturing efficiency which in turn reduces cost of the overall manufacturing process of the mouthpiece 46. The mouthpiece 46 is preferably made of plastic, however other materials are not beyond the scope of the present invention. Other materials for the mouthpiece 46 include, but are not limited to, ferrous alloys, non-ferrous alloys, ceramic materials, and composite materials and any mixtures thereof. Similar to the mouthpiece, the valve stem 44 is preferably made of plastic, but other materials are not beyond the scope of the present invention. Other materials for the valve stem 44 include, but are not limited to, ferrous alloys, non-ferrous alloys, ceramic materials, composite materials, and any mixtures thereof.

The pressurized container 34 preferably includes a liquid stored within the pressurized container 34 at a predetermined pressure. The liquid preferably includes a drug dispersed or dissolved therein such as salmeterol or fluticasone propionate.

Figure 4:
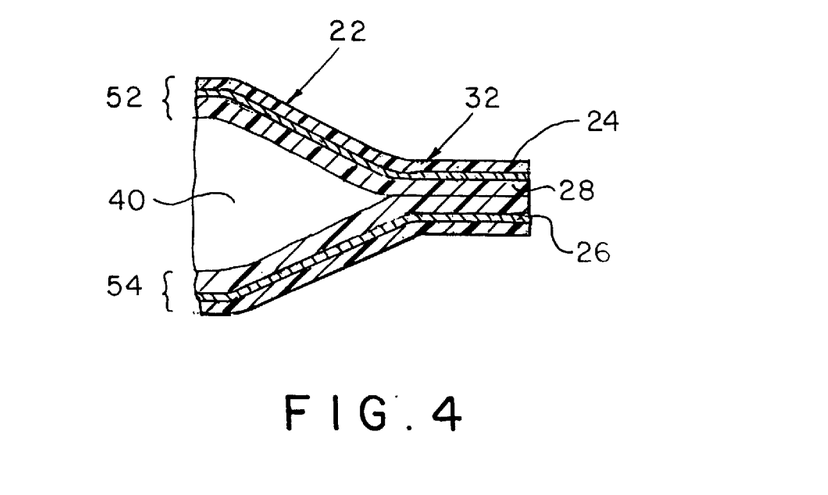
FIG. 4 is a cross-sectional view of the package for storing a pressurized container of the present invention.

In FIG. 4, a cross-sectional view of the package 22 is shown. Fin seams 32 include two peripheral edges 52, 54 of the flexible packaging material. The flexible packaging material comprises a first layer 24, a second layer 26, and a third, preferably heat sealable, layer 28 of material. The first layer 24 and third layer 28 are preferably made from polymers. The first layer 24 is preferably made out of polyester while the third layer 28 is preferably made out an ionomer resin. The second layer 26 is preferably made of a metal foil. In the preferred embodiment, the metal foil is made out of aluminum. In an alternative embodiment, the heat sealable layer is a polyethylene film.

As stated above, preferably, the protective layer (e.g., polyester) is adhesively laminated to the substrate (e.g., aluminum) and the substrate layer in turn is adhesively laminated to the heat sealable layer (e.g., the ionomer film or SURLYN™ (an ionomer resin) or a polyethylene film).

Preferred exemplary thicknesses of the three layers include a protective layer made of a polyester film having a thickness of 1 to 40, preferably 4 to 30, more preferably 10 to 23 microns, and most preferably 12 microns; a substrate layer made of aluminum having a thickness of 1 to 100, preferably 3 to 70, more preferably 5 to 50 microns, more preferably 6 to 20 microns, and most preferably 9 microns. For the heat sealable layer, an ionomer film is used having a preferred exemplary thicknesses of 1 to 100, preferably 5 to 70, more preferably 10–60, more preferably 25–55 microns, and most preferably 50 microns. In an alternative embodiment, a heat sealable layer of polyethylene film is used having a preferred thicknesses of 1 to 100, preferably 5 to 70, more preferably 10–60, more preferably 20–50 microns, and most preferably 50 microns.

Preferred exemplary embodiments include a polyester film as the protective layer having a thickness ranging from 12 to 23 microns. The polyester film is laminated to an aluminum foil as the substrate layer having a thickness ranging from 6 to 20 microns. The aluminum foil is laminated to a sealing film such as either an inomer film having a thickness ranging from 25 to 50 microns or a polyethylene film having a thickness ranging from 20 to 50 microns.

Alternative preferred embodiments include aluminum metalized polyester film laminated to a heat sealable layer as outlined above. Another embodiment includes a silicon oxide coplated polyester film laminated to a heat sealable layer as outlined above. Yet, in another embodiment, a polyester film as a protective layer having a thickness ranging from 12 to 30 microns is laminated to an aluminum foil substrate layer having a thickness ranging from 6 to 20 microns, the aluminum foil being laminated to a polyester film of 12 to 30 microns which is laminated to a heat sealable layer as outlined above. In another embodiment, a polypropylene film as a protective layer having a thickness ranging from 15 to 30 microns is laminated to an aluminum foil substrate layer having a thickness ranging from 6 to 20 microns, and the aluminum foil is laminated to a heat sealable layer as outlined above. The laminates of the present invention can be adhesively laminated or extrusion laminated.

The general structure for the preferred embodiment of the present invention is as follows: OUTSIDE ENVIRONMENT, POLYESTER FILM 24, ALUMINUM FOIL 26, IONOMER FILM 28, ENCLOSED VOLUME 40, IONOMER FILM 28, ALUMINUM FOIL 26, POLYESTER FILM 24, OUTSIDE ENVIRONMENT. (See FIG. 4.)

The lines in the drawings which show the boundaries between respective layers 24, 26, and 28 may be considered as adhesive layers if adhesives are used to join the respective layers. In other words, for example, the line separating protective layer 24 from the metal foil layer 26 may be interpreted as an adhesive, if an adhesive is used to join these layers 24, 26.

Figure 5:
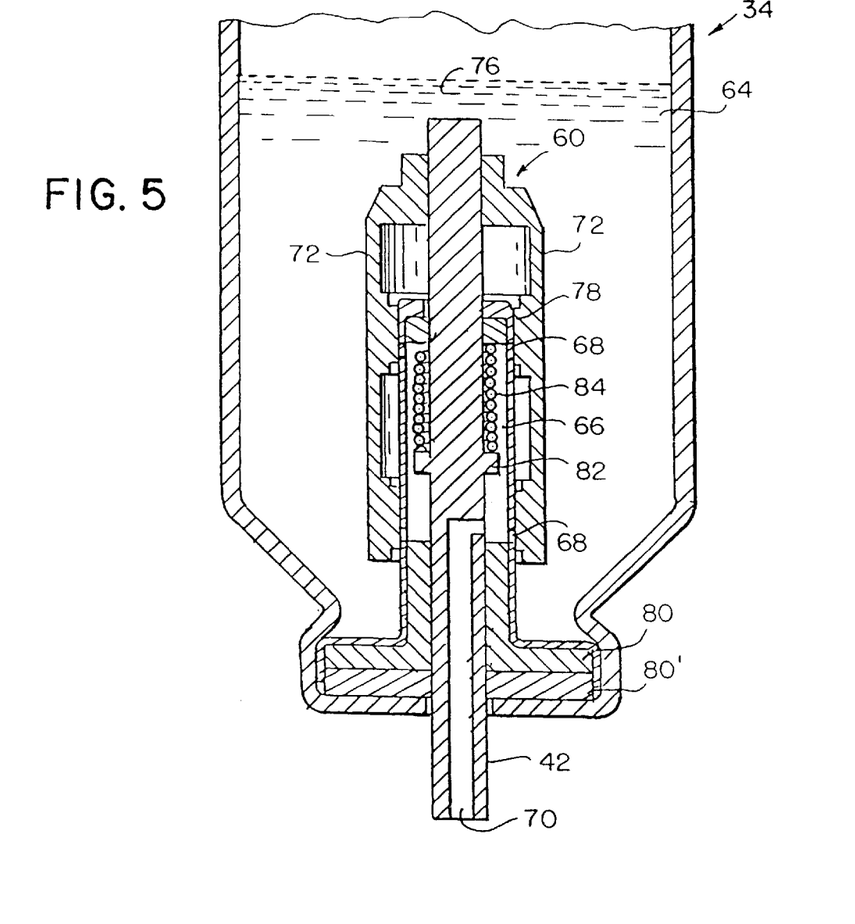
FIG. 5 is a cross-sectional view of the metering valve and container of the present invention.

FIG. 5 shows a fluid dispensing apparatus 36 containing a metered aerosol dispensing valve 60 which dispenses metered amounts of fluid material 76 from a reservoir 64. The fluid dispensing apparatus (or metered dose inhaler) may also be packaged as an article of manufacture (shown in FIGS. 2, 3, or 6) comprising an aerosol dispensing valve 60 of the present invention, an integral or additional dispensing apparatus, and a safe and therapeutically effective amount of a medicament in a pharmaceutically acceptable carrier, particularly a propellant. The medicament and carrier can also contain other medications and various excipients.

The packaging material of the article of manufacture may also have labeling 55 and information relating to the composition contained therein and/or printed thereon, such as by an adhesive label secured to the exterior of the flexible package. Additionally or alternatively, the article of manufacture of the present invention may have a brochure, report, notice, pamphlet, or leaflet 65 containing product information. This form of product information is sometimes, in the pharmaceutical industry, called the "package insert." A package insert 65 may be attached to or included with the article of manufacture. The package insert will usually be provided inside the box 74 but outside the flexible package. The package insert 65 and any article of manufacture labeling provides information relating to the composition and use of the product. This information and labeling provides various forms of information utilized by health care professionals and patients that describes the composition, the dosage, the use, and various other parameters of the medicament required by regulatory agencies, such as the United States Food and Drug Administration.

Figure 6:
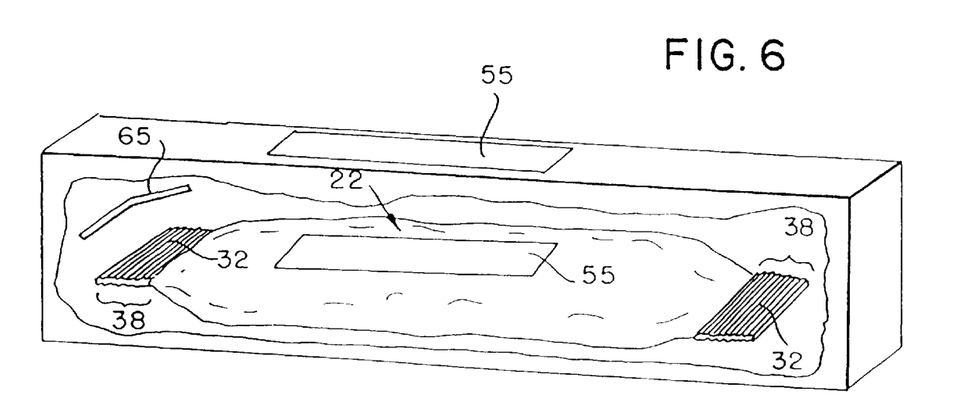
FIG. 6 is a side view of the second container with a product label which is placed over the wrapping means of the present invention.

FIGS. 5 and 6 show an article of manufacture including packaging material 22, a fluid dispensing apparatus or MDI 34 for dispensing metered amounts of fluid material 76 from a reservoir 64. The fluid dispensing apparatus 34 including a container 34 defining a reservoir 64, and a dispensing valve 60. The dispensing valve 60 includes a metering chamber body 62, defining a metering chamber 66 and having one or more metering chamber ports 68; and a stem 42 allowing for slideable movement within the metering chamber body 62. The stem 42 has a dispensing passage 70 and is connected to a sealing segment 72 allowing for slideable movement over the one or more metering chamber ports 68.

The stem 42 and sealing segment 72 are moveable such that in a first position the metering chamber 66 is fluidically isolated from the dispensing passage 70, and the metering chamber 66 is in fluidic communication with the reservoir 64 through the one or more metering chamber ports 68 and the dispensing passage 70. In a second position (as shown in FIG. 5), the metering chamber 66 is in fluidic communication with the dispensing passage 70; and the metering chamber 66 is fluidically isolated from the reservoir 64 by the sealing segment 72 occluding the one or more metering chamber ports 68 and the stem occluding the dispensing passage 70. Also shown in FIG. 5, is fluid material 76 containing a safe and effective medicament and a pharmaceutically acceptable carrier or diluent or propellant.

The dispensing valve 60 further includes an upper sealing sleeve 78 and lower sealing sleeves 80 and 80'. Stem 42 is positioned for slideable movement within metering chamber 7 through the lower and upper aperture containing lower sealing sleeves 80 and 80' and the upper sealing sleeve 78.

Flange 82 and spring 84 define the limits of travel for stem 42. Within these limits of travel, the stem 42 occupies an infinite number of positions which include the above mentioned first and second positions. In FIG. 5, stem 42 is biased toward the upper sealing sleeve 78 in the second position by physical force exerted by a user.

In FIG. 6, a box 74 encloses the container storage system 20. On the exterior of the box 74, a label 55 is disposed which provides information relating to the composition contained within the MDI. The label 55 may be located on any side of the box 74, that is most beneficial to the user. Further, as mentioned above, a package insert 65 may be disposed within the box 74 and outside the container storage system 20.

The present invention also provides a method of storing a container 34 including the steps of providing a flexible package 22 where the package 22 includes layers 24, 26, and 28 of material which are collectively impermeable to water vapor and permeable to vaporized propellant.

The method includes the step of filling the container 34 with the liquid propellant at a predetermined pressure and wrapping the container 34 with the flexible package 22 to form an enclosed volume 40 in which the first container 40 is disposed therein.

The method further includes sealing the flexible package 22 which in turn closes the enclosed volume 40, so that the flexible package 22 substantially prevents ingression of water vapor and particulate matter into said enclosed volume 40 while permitting egression of said vaporized propellant, whereby shelf life and performance of the drug and the propellant are increased. The packaged product can be stored for prolonged periods of time such as 1 month or more, 3 months or more or 6 months or more at temperatures such as 25°, 30° or 40° C. and at relative humidities of 60 or 75% while maintaining acceptable product properties.

The invention further includes method steps drawn to providing a material 50 for absorbing moisture in the enclosed volume 40 and disposed adjacent to the container 34.

Examples and Comparative Tests/Analysis

In order to evaluate the effectiveness of the method and package for storing a pressurized canister of the present invention, shelf-life tests were carried out upon packages 22 which contained MDIs such as salmeterol/HFC-134a inhalers, Albuterol/HFC-134a, and Fluticasone Propionate/HFC-134a inhalers. A first shelf-life test of Albuterol/HFC-134a inhalers showed that by placing an MDI into the package 22 containing silica gel desiccant or an absorbing mechanism 50, it was possible to substantially reduce the amount of moisture ingression (measured in Parts Per Million or PPM) into the inhaler after three months of storage at 40° C. and at 85% relative humidity. See Table 1.

TABLE 1

| Sample | Initial | 1 month @ 40° C./85% RH | 3 months @ 40° C./85% RH |
|---|---|---|---|
| Control (non overwrapped inhaler) | 35 ppm | 330 ppm | 446 ppm |
| Inhaler sealed in foil overwrap with 10 g silica gel desiccant | 35 ppm | 106 ppm | 178 ppm |
| Inhaler stored in Zantac Efferdose tube | 35 ppm | 158 ppm | 198 ppm |

Also included in Table 1 is data for MDIs which are stored in the prior art type tube containers. The prior art type tubes included a Zantac Efferdose tube. This type of tube is a plastic tube which contains silica gel desiccant. The silica gel is disposed in a resealable lid that closes the tube. This tube construction is similar to that used for a Schering product, Vanersil double strength.

A second test was performed and the results indicate that the reduction of moisture content within the package 22 can improve overall product performance of the liquid contained within the pressurized container 34, where the liquid includes an asthma treating drug and a propellant. In the second test, the experiment was performed where aged non-overwrapped salmeterol/HFC-134a inhalers were compared to MDIs provided in the package 22. The experiment included non-overwrapped inhalers which were stored for three months at either 30° C./60% relative humidity or 40° C./75% relative humidity. The non-overwrapped inhalers were then placed in a desiccator containing phosphorous pentoxide. The non-overwrapped inhalers were then tested for moisture content and fine particulate mass (FPM—the moisture sensitive product performance test over the period of inhaler drying). The results of this test are presented in Table 2.

TABLE 2

| | 30° C./60% RH | | 40° C./75% | |
|---|---|---|---|---|
| Time | Moisture content, PPM | FPM, Mcg | Moisture content, PPM | FPM, Mcg |
| Initial | 92 | 10.3 | 92 | 10.3 |
| 1 month non overwrapped | Not tested | Not tested | 412 | 8.2 |
| 3 month non overwrapped | 463 | 7.9 | 616 | 6.2 |
| 6 weeks drying | 233 | 8.9 | 298 | 7.4 |
| 13 weeks drying | 151 | 9.4 | 230 | 8.0 |

The data in Table 2 shows that loss and product performance (loss in FPM, for salmeterol) is directly related to change in moisture content. The results indicated that product performance of MDIs is reversible, although not 100% reversible. Therefore, if moisture causes loss in product performance, it is possible to retrieve and improve the product performance by removing moisture from the MDI during storage. Such is the result with the package 22 of the present invention.

A third comparative stability test at various elevated storage conditions was performed on a batch of Salmeterol/HFA134a Inhalers that were overwrapped shortly after manufacture and compared against a control of unoverwrapped inhalers from the same batch. The FPM and moisture determinations are summarized in Table 3 and 4. Table 3 shows the FPM over six months for the control group non-overwrapped MDIs compared to overwrapped MDIs (contained within the package 22 of the present invention). Table 4 shows the inhaler moisture content in Parts Per Million (or PPM) over six months for the control group of non-overwrapped meter dose inhalers compared to MDIs provided in the package 22 of the present invention.

The data in Table 3 shows that the fine particulate mass (FPM), measured in micrograms, of the MDIs provided in the package 22 of the present invention decreases at a substantially slower rate than that of the control group of non-overwrapped meter dose inhalers. The data in Table 4 shows that the moisture content in part per million over six months for the MDI provided in the package 22 of the present invention is less than the moisture content present adjacent to or within the MDIs which are not provided with any overwrap.

TABLE 3

| Time | 40° C./75% RH | | 25° C./60% RH | | 25° C./75% RH | |
|---|---|---|---|---|---|---|
| point (months) | control | wrapped | control | Wrapped | Control | wrapped |
| 0 | 9.4 | 9.4 | 9.4 | 9.4 | 9.4 | 9.4 |
| 1 | 7.8 | 8.6 | 8.4 | 8.6 | 8.4 | 8.7 |
| 3 | 6.0 | 7.4 | 8.3 | 8.5 | 8.0 | 8.3 |
| 6 | 6.2 | 7.7 | 7.5 | 7.8 | 7.2 | 7.8 |

TABLE 4

| Time | 40° C./75% RH | | 25° C./60% RH | | 25° C./75% RH | |
|---|---|---|---|---|---|---|
| point (months) | control | wrapped | control | Wrapped | Control | wrapped |
| 0 | 81 | 81 | 81 | 81 | 81 | 81 |
| 1 | 360 | 63 | 194 | 71 | 217 | 93 |
| 3 | 540 | 29 | 405 | 45 | 434 | 64 |
| 6 | 526 | 93 | 446 | 76 | 485 | 47 |

A fourth comparative test was performed on a control group of non-overwrapped MDIs containing fluticasone propionate/HFC-134a compared to MDIs of the same drug and propellant provided in the package 22 of the present invention. The MDIs of the present invention were manufactured and provided in the package 22 of the present invention shortly after the time of manufacture and placed on stability at various elevated storage conditions along side the control group of unwrapped inhalers from the same batch.

Table 5 of the fourth test summarizes the variation in the content uniformity at the six-month time period in addition to the moisture of the control group and the MDIs provided in the package 22 of the present invention. Table 5 shows the variation in content uniformity in percentage of the residual standard deviation (RSD) based on the values for a dose ex actuator obtained from ten cans at the end of use (final nominal use). This variation test was obtained over six months for the control group of non-overwrapped MDIs compared with MDIs provided in the package 22 of the present invention.

Table 6 shows the inhaler moisture content in parts per million or PPM over six months for the control group of non-overwrapped MDIs of the fluticasone propionate/HFC-134a type compared to MDIs of the same drug and propellant provided in the package 22 of the present invention. Table 5 demonstrates that the MDIs provided in the package 22 of the present invention have a substantially smaller standard deviation in product performance so that the MDI will typically have a consistent increased performance relative to non-overwrapped MDIs.

Table 6 further shows that the initial moisture content in parts per million for the MDIs 36 provided in the package 22 of the present invention significantly and substantially decreases while the moisture content of the control group of non-overwrapped MDIs substantially increases from the initial measurement of the moisture content.

TABLE 5

| Time point | 40° C./75% RH | | 30° C./75% RH | |
|---|---|---|---|---|
| (months) | control | wrapped | control | Wrapped |
| 0 | 6 | 6 | 6 | 6 |
| 3 | 14 | 5 | 11 | 5 |
| 4 | | | 12 | 5 |
| 6 | | | 12 | 9 |

*RSD (%) = percentage residual standard deviation based on the values for dose ex actuator obtained from 10 cans at the end of use (final nomial dose).

TABLE 6

| Time point | 40° C./75% RH | | 30° C./75% RH | |
|---|---|---|---|---|
| (months) | control | wrapped | control | Wrapped |
| 0 | 198 | 198 | 198 | 198 |
| 3 | 751 | 50 | 412 | 61 |
| 4 | | | 408 | 83 |
| 6 | | | 521 | 30 |

Table 7 shows the loss of HFC-134a (in grams) for wrapped Albuterol 134a MDI's stored for 14 months at 30° C./60% RH and 40° C./75% RH. The data in Table 7 is a mean of 5 determinations from 3 separate batches of MDI's.

TABLE 7

| | 40° C./75% RH | 30° C./60% RH |
|---|---|---|
| Loss of HFA134a from the can (g) | 0.4 | 0.7 |
| HFA134a remaining in the pack (g) | 0.1 | 0.2 |

The results of the above mentioned tests, outlined by Tables 1–4, prove that loss in fine particulate mass (FPM) of MDIs is directly related to moisture content adjacent or within an MDI. The results tabulated in Tables 5–7 prove that variation of the content uniformity at the end life of the wrapped MDIs of the present invention is substantially less than non-wrapped MDIs. Therefore, substantial increases in product performance of MDIs 36 are possible with the package 22 of the present invention which substantially reduces or eliminates the ingression of moisture or water vapor into the enclosed volume 40. Table 7 shows proof of the operation of the virtual one way valve mechanism.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A pressurized container storage system, comprising:
   a drug formulation comprising a mixture of a drug and a propellant;
   a pressurized container filled with said drug formulation at a predetermined pressure; and
   a flexible package for wrapping and sealing said pressurized container providing an enclosed volume in which said pressurized container is disposed, said flexible package being impermeable to water vapor and permeable to said propellant, said flexible package substantially preventing ingression of water vapor and particulate matter into said enclosed volume while permitting egression of said propellant.

2. The pressurized container storage system of claim 1, further comprising means for absorbing moisture in said enclosed volume.

3. The pressurized container storage system of claim 2, wherein said means for absorbing moisture in said enclosed volume includes a desiccant.

4. The pressurized container storage system of claim 3, wherein said desiccant includes at least one of zeolite, alumina, and silica gel.

5. The pressurized container storage system of claim 1, wherein said flexible package includes at least one heat sealable layer and at least one layer of a metal foil.

6. The pressurized container storage system of claim 5, wherein said metal foil includes at least one of aluminum, tin, iron, zinc, and magnesium.

7. The pressurized container storage system of claim 5, wherein said flexible package further includes a protective layer located on the outside of said package.

8. The pressurized container storage system of claim 7, wherein said protective layer includes a polyester film and said heat sealable layer includes an ionomer film.

9. The pressurized container storage system of claim 1, wherein said propellant includes a hydrofluroalkane.

10. The pressurized container storage system of claim 9, wherein said hydrofluroalkane is at least one of 1,1,1,2-tetrafluorethane and 1,1,1,2,3,3,3-heptafluoropropane.

11. The pressurized container storage system of claim 1, further comprising:
   a nozzle attached to said container, wherein said container and said nozzle form an MDI.

12. A method of storing a container comprising the steps of:
   providing a flexible package material, which is impermeable to water vapor and permeable to a propellant;
   filling a container with a drug formulation comprising a drug and said propellant at a predetermined pressure;
   wrapping said container with said flexible package material to form an enclosed volume in which said container is disposed therein; and
   sealing said flexible package which in turn closes said enclosed volume, said flexible package substantially preventing ingression of water vapor and particulate matter into said enclosed volume while permitting egression of said propellant from said enclosed volume.

13. The method of storing a pressurized container of claim 12, further comprising the step of providing a moisture absorbing material in said enclosed volume.

14. The method of storing a container of claim 12, wherein said sealing step includes heat sealing said flexible package material.

15. The method of storing a container of claim 12, further comprising the steps of:
   providing a nozzle; and
   attaching said nozzle to said container; said container, nozzle and valve form an MDI.

16. A packaged MDI, comprising:
   an MDI comprising a container and a drug metering valve, a pressurized drug formulation in said container comprising a propellant and a drug dispersed or dissolved in said propellant; and an overwrap of flexible material enclosing said MDI, said overwrap being made of a moisture impermeable material.

17. The MDI of claim 16, and further comprising a desiccant placed inside of said overwrap.

18. The MDI of claim 17, wherein said desiccant is a silica gel.

19. The MDI of claim 16, wherein said overwrap comprises a metallic foil.

20. The MDI of claim 16, wherein said propellant is HFC-134a, HFC-227 or a mixture thereof.

21. An article of manufacture comprising:

an aerosol dispensing apparatus for dispensing metered amounts of fluid material from a reservoir, the apparatus comprising a container defining a reservoir, and a dispensing valve, the dispensing valve comprising:

a metering chamber body defining a metering chamber and having one or more metering chamber ports; and a stem allowing for slideable movement within the metering chamber body, the stem having a dispensing passage and being connected to a sealing segment allowing for slideable movement over the one or more metering chamber ports, the sealing segment being moveable such that in a first position the metering chamber is fluidically isolated from the dispensing passage; and the metering chamber is in fluidic communication with the reservoir through the one or more metering chamber ports and the dispensing passage; and in a second position the metering chamber is in fluidic communication with the dispensing passage; and the metering chamber is fluidically isolated from the reservoir by the sealing segment occluding the one or more metering chamber ports;

a drug formulation located within said aerosol dispensing apparatus comprising a safe and effective medicament and a pharmaceutically acceptable propellant; and a flexible package for wrapping and sealing said container providing an enclosed volume in which said pressurized container is disposed, said flexible package being impermeable to water vapor and permeable to said propellant, said flexible package substantially preventing ingression of water vapor and particulate matter into said enclosed volume while permitting egression of said propellant.

22. The article of manufacture of claim 21, further comprising a brochure disclosing product information.

23. The article of manufacture of claim 21, further comprising a container for enclosing said flexible package.

24. A method of improving a product performance comprising the steps of:

providing a flexible package material made of at least one heat sealable layer, at least one layer of a metal foil, and a protective layer; said flexible package material being impermeable to water vapor and permeable to a propellant;

filling a container with a drug formulation comprising a drug and said propellant at a predetermined pressure;

wrapping said container with said flexible package material to form an enclosed volume in which said container is disposed therein; and sealing said flexible package which in turn closes said enclosed volume, said flexible package substantially preventing ingression of water vapor and particulate matter into said enclosed volume while permitting egression of said propellant from said enclosed volume.

25. The method of improving product performance of claim 24, further comprising the step of providing a moisture absorbing material in said enclosed volume.

26. The method of improving product performance of claim 24, wherein said sealing step includes heat sealing said flexible package material.

27. The method of improving product performance of claim 24, further comprising the steps of:

providing a nozzle;

providing a valve; and attaching said nozzle and said valve to said container; said container, valve, and nozzle and valve form an MDI.

28. The method of improving product performance of claim 24, wherein the steps of providing a protective layer and a heat sealable layer include the steps of providing a polyester film and an ionomer film.

29. The method of improving product performance of claim 24, wherein the step of filling said container includes filling the container with a hydrofluroalkane.

30. The method of improving product performance of claim 29, wherein the step of filling said container includes filling said container with at least one of 1,1,1,2-tetrafluorethane and 1,1,1,2,3,3,3-heptafluoropropane.

* * * * *